United States Patent
Bao et al.

(12)

(10) Patent No.: US 7,094,582 B2
(45) Date of Patent: Aug. 22, 2006

(54) CELL-FREE PRODUCTION OF GLUCOSAMINE

(75) Inventors: Wuli Bao, Forsyth, IL (US); Thomas P. Binder, Decatur, IL (US); Paul D. Hanke, Urbana, IL (US); Leif Solheim, Decatur, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 457 days.

(21) Appl. No.: 10/671,886

(22) Filed: Sep. 29, 2003

(65) Prior Publication Data

US 2005/0042734 A1   Feb. 24, 2005

Related U.S. Application Data

(60) Provisional application No. 60/414,410, filed on Sep. 30, 2002.

(51) Int. Cl.
*C12P 19/28*  (2006.01)
*C07H 5/06*   (2006.01)

(52) U.S. Cl. .......................... 435/85; 435/84; 536/55.2

(58) Field of Classification Search .................. 435/84, 435/85; 536/55.2
See application file for complete search history.

(56) References Cited

U.S. PATENT DOCUMENTS

| | | | |
|---|---|---|---|
| 5,587,363 A | 12/1996 | Henderson | |
| 5,679,244 A | 10/1997 | Tettman et al. | |
| 5,702,939 A * | 12/1997 | Fujishima et al. | 435/233 |
| 5,843,919 A | 12/1998 | Burger | |
| 6,162,787 A | 12/2000 | Sorgente et al. | |
| 6,372,457 B1 * | 4/2002 | Berry et al. | 435/72 |
| 6,444,878 B1 * | 9/2002 | Donaldson et al. | 800/300 |
| 2003/0044939 A1 * | 3/2003 | Berry et al. | 435/84 |

\* cited by examiner

*Primary Examiner*—Herbert J. Lilling
(74) *Attorney, Agent, or Firm*—Kirkpatrick & Lockhart Nicholson Graham LLP

(57) ABSTRACT

Methods for cell-free production of glucosamine from starch, maltodextrin or glycogen or from fructose and a source of amino groups are disclosed. Also disclosed are cellular extracts comprising glucosamine-6-phosphate synthase activity, as well as a cellular extract comprising glucosamine-6-phosphate deaminase.

10 Claims, No Drawings

CELL-FREE PRODUCTION OF GLUCOSAMINE

CROSS-REFERENCE TO RELATED APPLICATIONS

This application claims benefit of priority to U.S. Provisional Application No. 60/414,410, filed Sep. 30, 2002, and which is hereby incorporated by reference in its entirety.

BACKGROUND OF THE INVENTION

1. Field of the Invention

The invention relates to methods for the cell-free production of glucosamine from starch, maltodextrin or glycogen; or from fructose and a source of amino groups.

2. Related Art

Glucosamine is an amino sugar, which is found in many naturally occurring polysaccharides. Glucosamine has found increasing use in the treatment of osteoarthritis and other conditions. Glucosamine has traditionally been produced by the hydrolysis of shellfish exoskeleton (chitin), which is composed of poly(N-acetyl-D-glucosamine). The availability of raw material, however, is becoming increasingly limited. More recently, the production of glucosamine by microbial fermentation has been disclosed. U.S. Pat. No. 6,372,457 discloses fermentation of microorganisms that have been genetically modified in a pathway related to glucosamine or glucosamine-6-phosphate, in order to produce high levels of glucosamine.

There remains a need in the art for a method of producing glucosamine using abundant and inexpensive starting materials.

BRIEF SUMMARY OF THE INVENTION

The present invention relates to a cell-free method of producing glucoasamine-6-phosphate from starch, maltodextrin or glycogen comprising incubating starch, maltodextrin or glycogen with glutamine in a reaction mixture comprising a cellular extract comprising glucosamine-6-phosphate synthase and/or glucosamine-6-phosphate deaminase activity.

In a further embodiment, the present invention relates to a cell-free method of producing glucosamine comprising incubating fructose and a source of amino groups in a reaction mix comprising a cellular extract comprising glucosamine-6-phosphate synthase and/or glucosamine-6-phosphate deaminase activity.

An additional embodiment of the invention relates to a cell free method of producing glucosamine-6-phosphate from starch, glycogen or maltodextrin comprising incubating starch, glycogen or maltodextrin with glutamine in a reaction mix containing a phosphorylase, phosphoglucomutase, glucose-6-phosphate isomerase (also known as phosphoglucose isomerase and phosphoglucoisomerase), glucose-1,6-bisphosphate and a cellular extract comprising glucosamine-6-phosphate synthase activity.

A further embodiment of the invention relates to a cell free method of producing glucosamine-6-phosphate from starch, glycogen or maltodextrin comprising incubating starch, glycogen or maltodextrin with an ammonium source in a reaction mix containing a phosphorylase, phosphoglucomutase, phosphoglucose isomerase, glucose-1,6-bisphosphate and a cellular extract comprising glucosamine-6-phosphate deaminase activity.

In another embodiment, the present invention relates to a cell-free method of producing glucosamine comprising incubating fructose and glutamine in a reaction mix comprising a cellular extract comprising glucosamine-6-phosphate synthase.

In a further embodiment, the present invention relates to a cell-free method of producing glucosamine comprising incubating fructose and an ammonium source in a reaction mix comprising a cellular extract comprising glucosamine-6-phosphate deaminase.

An additional embodiment of the present invention relates to a cellular extract comprising glucosamine-6-phosphate synthase and/or glucosamine-6-phosphate deaminase activity, wherein said extract is prepared by collecting precipitate produced by ammonium sulfate precipitation between 30% and 60% ammonium sulfate saturation.

In another embodiment, the present invention relates to a cell-free method of producing glucosamine comprising incubating glucosamine-6-phosphate with a phosphatase in a reaction mix.

DETAILED DESCRIPTION OF THE INVENTION

An enzymatic pathway for the production of glucosamine from starch, maltodextrin or glycogen has been identified. The terminal glucosyl residue of starch or glycogen can be released from the polymer and transferred to a phosphate molecule by phosphorylase, an enzyme that cleaves the glycosidic bond to form glucose-1-phosphate. Using phosphoglucomutase in the presence of the activator glucose-1,6-bisphosphate, the product glucose-1-phosphate is converted to glucose-6-phosphate, which in turn can be transformed to fructose-6-phosphate with the enzyme phosphoglucose isomerase. The enzyme glucosamine-6-phosphate synthase (glucosamine:fructose-6-phosphate amidotransferase) makes glucosamine-6-phosphate by transferring an amino group from glutamine to fructose-6-phosphate. Alternatively, the enzyme glucosamine-6-phosphate deaminase can also form glucosamine by transferring an amino group to fructose-6-phosphate. Finally, phosphatase catalyzes the removal of the phosphate group from glucosamine-6-phosphate to produce glucosamine. The phosphate released from glucosamine-6-phosphate can be used for further cleavage of starch, maltodextrin or glycogen by phosphorylase.

Glucosamine-6-phosphate synthase catalyzes the synthesis of glucoasamine-6-phosphate from fructose-6-phosphate and the amino group of glutamine. Since the phosphate group of fructose-6-phosphate remains intact during the reaction and is not involved in the aminotransferase reaction, the enzyme is capable of functioning with the closely related compound fructose as a substrate.

Glucosamine-6-phosphate deaminase can also catalyze the synthesis of glucosamine-6-phosphate from fructose-6-phosphate and ammonium. As stated above, the phosphate group of fructose-6-phosphate remains intact during the reaction and is not involved in the aminotransferase reaction, and the enzyme is capable of functioning with the closely related compound fructose as a substrate at a low rate.

In a first embodiment of the present invention, a cellular extract is prepared which contains glucosamine-6-phosphate synthase and/or glucosamine-6-phosphate deaminase activity for use in the production of glucosamine from starch, glycogen, maltodextrin or other substrates. The cellular extract can be prepared from any cell which contains glucosamine-6-phosphate synthase and/or glucosamine-6-phosphate deaminase activity. Preferably, the cellular extract is prepared from cells known to contain the enzyme glucosamine-6-phosphate synthase and/or glucosamine-6-phosphate deaminase. The cells can be eukaryotic or prokaryotic cells. Eukaryotic cells can be mammalian cells or yeast cells. Prokaryotic cells can be bacterial cells. In one preferred embodiment, the cellular extract is prepared from *E. coli* cells. The cells can be cultured cells or cells obtained from a tissue or organ. Cellular extract can be prepared from any amount of cells, depending on the amount of glucosamine-6-phosphate synthase and/or glucosamine-6-phosphate deaminase activity that is desired.

The cellular extract can be prepared by any method for making extracts which is known to preserve enzymatic activity. Preferably, the extract is prepared by disrupting the cells, for example by sonication, removing cellular debris and fractionating the resultant extract by ammonium sulfate precipitation to at least partially purify the glucosamine-6-phosphate synthase and/or glucosamine-6-phosphate deaminase activity. In a preferred embodiment, the fraction found in the precipitate formed between 30% and 60% ammonium sulfate saturation is used. More preferably, either the fraction found in the precipitate formed between 30% and 50% or the fraction found in the precipitate formed between 40% and 60% ammonium sulfate saturation can be used. Although the fractions overlap to a great degree, the fraction found in the precipitate formed between 30% and 50% ammonium sulfate saturation will contain a greater deaminase activity, and the fraction found in the precipitate formed between 40% to 60% ammonium sulfate saturation will contain a higher level of synthase activity. The precipitate containing the glucosamine-6-phosphate synthase or deaminase activity can be resuspended in any buffer that preserves synthase or deaminase activity. For example buffers such as, but not limited to, 100 mM Tris, pH 7.5; 100 mM NaCl or 50 mM Tris, pH 7.5; 100 mM NaCl may be used.

The preparation of cellular extract, including fractionation, can be monitored by measuring glucosamine-6-phosphate synthase and/or glucosamine-6-phosphate deaminase activity. Enzyme activity can be measured by any method known in the art. In one embodiment, the enzyme activity can be measured using fructose-6-phosphate and glutamine or an ammonium source as substrates and measuring production of glucosamine-6-phosphate. In another embodiment, the glucosamine-6-phosphate synthase activity can be coupled to glutamate dehydrogenase activity such that glutamate, which is a product of the synthase reaction, is deaminated while the coenzyme $NADP^+$ is reduced to NADPH. Synthase activity can therefore be measured by detecting production of NADPH by spectrophotometry at a wavelength of 340 nm. In this embodiment, a typical reaction mix for measuring synthase activity comprises:

100 mM potassium phosphate, pH 7.5;
50 mM KCl;
5 mM fructose-6-phosphate;
5 mM glutamine;
2 mM EDTA;
0.5 mM $NADP^+$
30 U glutamate dehydrogenase; and
10% *E. coli* extract (1 mg/ml total protein).

In another embodiment, glucosamine-6-phosphate deaminase can be measured using glucosamine-6-phosphate as a substrate and measuring fructose-6-phosphate.

In another embodiment glucosamine-6-phosphate activity can be coupled to glucose-6-phosphate dehydrogenase activity such that the fructose-6-phosphate is converted to glucose-6-phosphate by phosphoglucose isomerase such that glucose-6-phosphate is oxidized to D-glucono-1,5-lactone-6-phosphate and $NADP^+$ is reduced to NADPH. Activity can therefore be measured by detecting production of NADPH by spectrophotometry at a wavelength of 340 nm. In this embodiment, a typical reaction mix for measuring the deaminase comprises:

100 mM Tris-HCl pH 7.8
5 mM $NADP^+$
10 mM $MgCl_2$
5 mM glucosamine-6-phosphate
5 U phosphoglucose isomerase
0.4 U glucose-6-phosphate dehydrogenase
enzyme extract In a preferred embodiment, the cellular extract that is prepared will have a glucosamine-6-phosphate synthase and/or glucosamine-6-phosphate deaminase specific activity of at least about 0.01 U/mg protein, more preferably about 0.1 U/mg protein to about 1.0 U/mg protein, most preferably about 0.2 U/mg protein.

In a further embodiment of the present invention, a cell-free method is used to produce glucosamine-6-phosphate from starch, maltodextrin or glycogen using cellular extract comprising glucosamine-6-phosphate synthase and/or glucosamine-6-phosphate deaminase activity. In this embodiment, the starch, maltodextrin or glycogen is incubated with glutamine or an ammonium source in a reaction mixture comprising the cellular extract. The starch can be any starch, including, but not limited to, soluble starch, corn starch, potato starch, rice starch, tapioca starch or wheat starch. Maltodextrins are non-sweet, nutrative polysaccharide polymers that consist of D-glucose units linked primarily by (alpha)-1,4 bonds. Maltodextrins are formed from the partial hydrolysis of starch. The starch can be any starch, including, but not limited to soluble starch, corn starch, potato starch, rice starch, tapioca starch or wheat starch. The maltodextrins that may be employed by this invention include, but are not limited to, maltodextrin 10. The glycogen can be from any source, including, but not limited to, rabbit liver, bovine liver, mussel or oyster. The cellular extract preferably is present in the reaction mixture at a concentration of about 1% to about 20%, more preferably about 5% to about 15%, most preferably about 10%. The starch, maltodextrin or glycogen preferably is present in the reaction mix at a concentration of about 0.05% to about 2.0%, more preferably about 0.1% to about 1.0%, most preferably about 0.2%. The incubation preferably occurs at a temperature of about 20° C. to about 50° C., more preferably about 25° C. to about 40° C., most preferably about 30° C. The reaction preferably proceeds for a time period of about 10 minutes to about 2 hours, more preferably for about 30 minutes to about 1.5 hours, most preferably about 1 hour.

In a preferred embodiment, glucosamine-6-phosphate synthase and accessory factors needed to produce glucosamine-6-phosphate from starch, maltodextrin or glycogen are added to the reaction mix. This includes one or more of the enzymes phosphorylase, phosphoglucomutase and phosphoglucose isomerase and the activator glucose-1,6-bisphosphate. The reaction mix contains a phosphate source; starch, maltodextrin or glycogen, KCl, glutamine, a magnesium source; glucose-1,6-bisphosphate; a phosphorylase; phosphoglucomutase; phosphoglucose isomerase and the cellular extract. The phosphate source may include, but is not limited to, potassium phosphate, sodium phosphate, magnesium phosphate, calcium phosphate, phosphoric acid or ammonium phosphate. The magnesium source may include, but is not limited to magnesium chloride, magnesium sulfate and magnesium citrate. In one preferred embodiment, the reaction mix comprises:

100 mM potassium phosphate, pH 7.0;
0.2% soluble starch;
50 mM KCl;
5 mM glutamine;
5 mM $MgCl_2$;
1 mM glucose-1,6-bisphosphate;

10 U/ml phosphorylase a;
5 U/ml phosphoglucomutase;
25 U/ml phosphoglucose isomerase; and
10% *E. coli* extract (1 mg/ml total protein).

In another preferred embodiment, glucosamine-6-phosphate deaminase and accessory factors needed to produce glucosamine-6-phosphate from starch, maltodextrin or glycogen are added to the reaction mix. This includes one or more of the enzymes phosphorylase, phosphoglucomutase and phosphoglucose isomerase and the activator glucose-1,6-bisphosphate. The reaction mix contains a phosphate source; starch, maltodextrin or glycogen, KCl, an ammonium source, a magnesium source; glucose-1,6-bisphosphate; a phosphorylase; phosphoglucomutase; phosphoglucose isomerase and the cellular extract. The phosphate source may include, but is not limited to, potassium phosphate, sodium phosphate, magnesium phosphate, calcium phosphate, phosphoric acid or ammonium phosphate. The magnesium source may include, but is not limited to magnesium chloride, magnesium sulfate and magnesium citrate. The ammonium source may include, but is not limited to, ammonium sulfate, ammonium phosphate, ammonium chloride or ammonium hydroxide. In one preferred embodiment, the reaction mix comprises:

100 mM potassium phosphate, pH 7.5;
0.2% maltodextrin 10;
50 mM KCl;
50 mM ammonium sulfate;
10 mM $MgCl_2$;
1 mM glucose-1,6-bisphosphate;
10 U/ml phosphorylase a;
16U/ml phosphoglucomutase;
25 U/ml phosphoglucose isomerase; and
40–60% ammonium sulfate cut containing glucosamine-6-phosphate deaminase.

Following the production of glucosamine-6-phosphate as described above, it is desirable to remove the phosphate group to produce glucosamine. Therefore, a further embodiment of the present invention is a cell-free method of producing glucosamine comprising incubating glucosamine-6-phosphate with a phosphatase in a reaction mix. The phosphatase can be any phosphatase that is effective for dephosphorylating from glucosamine-6-phosphate. Examples include shrimp alkaline phosphatase, bovine intestinal alkaline phosphatase and bacterial alkaline phosphatase. The incubation preferably occurs at a temperature of about 20° C. to about 50° C., more preferably about 25° C. to about 40° C., most preferably about 30° C. The reaction preferably proceeds for a time period of about 10 minutes to about 2 hours, more preferably for about 10 minutes to about 1 hour, most preferably about 10 minutes. The reaction mix comprises a buffer suitable for the dephosphorylation step to occur, preferably an alkaline buffer, for example Tris, pH 8.5. In a particular embodiment, the reaction mix comprises:

20 mM glucosamine-6-phosphate;
5 U/ml shrimp alkaline phosphatase;
50 mM Tris, pH 8.5; and
5 mM $MgCl_2$.

In yet another preferred embodiment, glucosamine-6-phosphate synthase is used to produce glucosamine directly from fructose. The reaction mix contains a fructose, glutamine, KCl and the cellular extract. In one preferred embodiment, the reaction mix comprises:

20 mM fructose;
50 mM KCl;
5 mM glutamine; and
10% *E. coli* extract (1 mg/ml total protein).

In a further preferred embodiment, glucosamine-6-phosphate deaminase is used to produce glucosamine directly from fructose. The reaction mix contains a fructose, ammonium, KCl and the cellular extract. In one preferred embodiment, the reaction mix comprises:

20 mM fructose;
50 mM KCl;
250 mM ammonium sulfate; and
10% *E. coli* extract (1 mg/ml total protein).

An additional embodiment of the present invention is a cell-free method of producing glucosamine comprising incubating fructose and a source of amino groups in a reaction mix comprising cellular extract having glucosamine-6-phosphate synthase activity and/or glucosamine-6-phosphate deaminase activity. The cellular extract preferably is present in the reaction mixture at a concentration of about 1% to about 20%, more preferably around 5% to about 15%, most preferably about 10%. The fructose preferably is present in the reaction mix at a concentration of about 1 mM to about 100 mM, more preferably about 10 mM to about 50 mM, most preferably about 20 mM. The source of amino groups can be any compound capable of donating amino groups to the enzymatic reaction. Examples include glutamine and ammonium salts. When glutamine is used, it preferably is present in the reaction mix at a concentration of about 1 mM to about 100 mM, more preferably about 2 mM to about 50 mM, most preferably about 5 mM. In a preferred embodiment, the reaction mix comprises:

100 mM Tris, pH 7.5;
50 mM KCl;
20 mM fructose;
5 mM glutamine; and
10% *E. coli* extract (1 mg/ml total protein).

The incubation preferably occurs at a temperature of about 20° C. to about 50° C., more preferably about 25° C. to about 40° C., most preferably about 30° C. The reaction preferably proceeds for a time period of about 10 minutes to about 2 hours, more preferably for about 15 minutes to about 1 hour, most preferably about 20 minutes. When an ammonium salt is used as the source of amino groups, appropriate salts include, without limitation, ammonium sulfate, ammonium phosphate, ammonium chloride and ammonium hydroxide. The ammonium preferably is present at a concentration of about 10 mM to about 1000 mM, more preferably about 50 mM to about 500 mM, most preferably about 250 mM. In a preferred embodiment, the reaction mix comprises:

100 mM Tris, pH 7.5;
50 mM KCl;
20 mM fructose;
250 mM ammonium sulfate; and
10% *E. coli* extract (1 mg/ml total protein).

The following examples are illustrative, but not limiting, of the method and compositions of the present invention. Other suitable modifications and adaptations of the variety of conditions and parameters normally encountered in enzymatic production of chemicals and which are obvious to those skilled in the art are within the spirit and scope of the invention.

EXAMPLE 1

Isolation and Assay of Glucosamine-6-Phosphate Synthase from *E. coli* Cells

*E. coli* cells from frozen vials were inoculated into a flask culture containing 12 L fermentation seed medium. The medium contained the following chemicals (g/L): corn steep liquor, 10; KH$_2$PO$_4$, 2.5; MgSO$_4$.7H$_2$O, 2.0; (NH$_4$)$_2$SO$_4$, 0.5; citric acid, 0.192; FeSO$_4$.7H$_2$O, 0.03; MnSO$_4$.H$_2$O, 0.021; antifoam 6000K, 0.5; dextrose, 84. The seed fermentor was operated at 39° C. at an agitation speed of 700 rpm and an airflow of 3.5 LPM. The pH of the fermentation was maintained at 6.9 with 21% NH$_4$OH. After 24 hours of growth, the broth was centrifuged and the pellets were resuspended in extract buffer (100 mM Tris, pH 7.5; 100 mM NaCl). The cells were centrifuged and the pellets were resuspended in the extract buffer at a concentration of OD660 about 200. Sonication was applied to the cells four times for 30 seconds with intermissions of 1 minute. Centrifugation was used to separate the cell debris and the supernatant was maintained as enzyme extract. Ammonium sulfate was added to the extract to 226 g/L (40% saturation) and the extract was centrifuged. 120 g/L ammonium sulfate (60% saturation) was added to the supernatant. After centrifugation, the pellets were collected and resuspended in the extract buffer. Most of the glucosamine-6-phosphate activity was in this fraction.

Glucosamine-6-phosphate synthase activity was assayed in the extract by coupling the activity with glutamate dehydrogenase, which deaminates the synthase product glutamate and reduces coenzyme NADP$^+$ to NADPH. The amount of NADPH generated in the reaction was monitored with an absorbance spectrophotometer at a wavelength of 340 nm. The enzyme specific activity was calculated based on the initial rate of absorbance change after addition of *E. coli* extract. The assay contained the following:

100 mM potassium phosphate, pH 7.5;
50 mM KCl;
5 mM fructose-6-phosphate;
5 mM glutamine;
2 mM EDTA;
0.5 mM NADP;
30 U glutamate dehydrogenase; and
10% *E. coli* extract (1 mg/ml total extract).

There was about 0.02 U/mg protein of glucosamine-6-phosphate synthase activity in the crude extract and 0.2 U/mg protein of the activity after the ammonium sulfate precipitation. The production of glucosamine-6-phosphate was also confirmed by liquid chromatography analysis.

EXAMPLE 2

Production of Glucosamine-6-Phosphate from Starch by Coupling Enzyme Reactions

In this example, the cell-free production of glucosamine-6-phosphate from starch was accomplished by coupling several enzymes into one reaction mix. The reaction mix contained:

100 mM potassium phosphate, pH 7.0;
0.2% soluble starch;
50 mM KCl;
5 mM glutamine;
5 mM MgCl$_2$;
1 mM glucose-1,6-bisphosphate;
10 U phosphorylase a (Sigma);
5 U phosphoglucomutase (Sigma);
25 U phosphoglucose isomerase (Sigma); and
10% *E. coli* extract (1 mg/ml total protein).

The starch was dissolved in water by heating to boiling. The reaction mix was incubated in a water bath at 30° C. for 1 hour and analyzed for glucosamine-6-phosphate. Controls consisted of reaction mixes containing heat inactivated *E. coli* extract or without the starch solution.

HPLC data showed that glucosamine-6-phosphate (175 µg/ml) was produced in the reaction. Glucose-6-phosphate and fructose-6-phosphate were also detected in the reaction mix. In the control reactions containing the heat inactivated *E. coli* extract or without starch, glucosamine-6-phosphate was not detected.

EXAMPLE 3

Production of Glucosamine-6-Phosphate from Maltodextrin and Glutamine by Coupling Enzyme Reactions In this example, the cell free production of glucosamine-6-phosphate from maltodextrin was accomplished by coupling several enzymes into one reaction mix. The reaction mix contained:

100 mM potassium phosphate, pH 7.5
0.2% maltodextrin 10
50 mM KCl
5 mM glutamine
10 mM MgCl$_2$
1 mM glucose-1,6-bisphosphate
10 U phosphorylase a (Sigma);
16 U phosphoglucomutase (Sigma);
25 U phosphoglucose isomerase (Sigma);
100 µL 40–60% (NH$_4$)$_2$SO$_4$ cut The reaction was incubated at 30° C. for 1 hour and analyzed for glucosamine-6-phosphate. Control reactions were included. These consisted of reactions without *E. coli* extract and without maltodextrin. HPLC data showed that 130 µg/ml glucosamine-6-phosphate was produced by this reaction. The control reactions did not produce any glucosamine-6-phosphate. When 100 µl of crude *E. coli* extract was substituted, for the 40–60% ammonium sulfate cut 48 µg/ml glucosamine-6-phosphate was produced.

EXAMPLE 4

Production of Glucosamine-6-Phosphate from Maltodextrin and Ammonium Sulfate by Coupling Enzyme Reactions This example illustrates the cell free production of glucosamine-6-phosphate from maltodextrin. The reaction was accomplished by the coupling of several enzymes into one reaction mix. The reaction contained:

100 mM potassium phosphate, pH 7.5
0.2% maltodextrin 10
50 mM KCl
50 mM (NH$_4$)$_2$SO$_4$
10 mM MgCl$_2$
1 mM glucose-1,6-bisphosphate
10 U phosphorylase a (Sigma);
16 U phosphoglucomutase (Sigma);
25 U phosphoglucose isomerase (Sigma);
100 µl 40–60% (NH$_4$)$_2$SO$_4$ cut
H2O to bring to 1 ml total volume The reaction was incubated for 1 hour and analyzed for glucosamine-6-phosphate. The controls consisted of reactions without *E. coli* extract and without maltodextrin. HPLC data showed that glucosamine-6-phosphate (111 µg/ml) was produced in this reaction. In the control reactions, no glucosamine-6-phosphate was produced.

EXAMPLE 5

Production of Glucosamine from Glucosamine-6-Phosphate by Phosphatases

In this example the cell-free production of glucosamine from glucosamine-6-phosphate was accomplished in the following reaction mix:

20 mM glucosamine-6-phosphate (Sigma);
5 U shrimp alkaline phosphatase (Sigma);
50 mM Tris, pH 8.5; and
5 mM $MgCl_2$.

The 1 ml reaction mix was incubated at 30° C. for 10 minutes and analyzed for glucosamine by HPLC. Glucosamine (2.8 mg/ml, 13 mM) was detected in the reaction mix. Glucosamine was not detected in the control reactions that contained no substrate glucosamine-6-phosphate or no enzyme phosphatase.

EXAMPLE 6

Production of Glucosamine from Fructose and Glutamine

Enzyme reactions were set up to produce glucosamine from fructose and glutamine. One ml reactions containing 100 mM Tris pH 7.5; 50 mM KCl; 20 mM fructose; 5 mM glutamine; and 0.1 ml E. coli extract (1 mg/ml total protein) were incubated at 30° C. for 20 minutes, and the samples were analyzed for glucosamine. Reactions with heat inactivated E. coli extract were included as controls.

The analytical results showed that 92.5 µg glucosamine was made from fructose and glutamine in 20 min. The specific activity for this reaction was 23 mmol/min/mg protein, which was 10 times less than the activity with the natural substrates fructose-6-phosphate and glutamine. Glucosamine was not detectable in the controls containing heat inactivated extract.

EXAMPLE 7

Production of Glucosamine from Fructose and Ammonium

Enzyme reactions were set up to produce glucosamine from fructose and ammonium. One ml reactions containing 100 mM Tris pH 7.5; 50 mM KCl; 20 mM fructose; 250 mM ammonium sulfate; and 0.1 ml E. coli extract (1 mg/ml total protein) were incubated at 30° C. for 20 minutes. The samples were analyzed for glucosamine production by HPLC. Reactions with heat inactivated E. coli extract were included as controls.

Results showed that in 20 minute reactions, 6 µg/ml glucosamine was made from fructose and ammonium. The specific activity for this reaction was 1.5 mmol/min/mg protein, which is 130 times less than the activity with the natural substrates fructose-6-phosphate and glutamine. Glucosamine was not detected in the control reactions containing heat inactivated extract.

EXAMPLE 8

Cloning of nagB Gene into pKK223-3

For the construction of the nagB expression plasmid, EcoRI and HindIII restriction sites were introduced at the front of the translation start codon of nagB and downstream of the translation stop codon of nagB, respectively. The primers used for polymerase chain reaction (PCR) were 5'-CATCTAGAATTCATGAGACTGATC-CCCCTGACTACC-3' (SEQ ID NO: 1) and 5'-CATCTAAAGCTTCAAGGAGCCAGGGCAGGG-3' (SEQ ID NO: 2). PCR reactions were carried out based on a protocol from a PCR reaction kit from Invitrogen. The reaction consisted of 1 ng E. coli genomic DNA, 0.3 um of each primer, dNTP mix (0.3 um of each dNTP), 1 mM MgSO4, and 1 U of platinum Pfx DNA polymerase in 1× Pfx amplification buffer. The 800-bp PCR product was recovered by 0.8% agarose gel electrophoresis, digested with Eco RI and HindIII and ligated into the EcoRI-HindIII sites of plasmid pKK223-3. The plasmid was then transformed into E. coli strain DH5a. Overexpression of nagB gene product was induced by IPTG when grown in LB medium The activity of glucosamine-6-phosphate deaminase was assayed in a mixture containing 50 mM Tris buffer, pH 7.8, 5 mM glucosamine-6-phosphate, 5 U glucosamine-6-phosphate isomerase, 5 U glucose-6-phosphate dehydrogenase, 1 mM NADP and enzyme extract. The activity was followed by the change of absorbance at 340 nm. The activity of glucosamine-6-phosphate deaminase in the extract of the strain containing the nagB expression plasmid was about 50 times higher than the extract from the host strain E. coli DH5a.

EXAMPLE 9

Production of Glucosamine from Fructose and Ammonium

Enzyme reactions were performed to produce glucosamine from fructose and ammonium in the presence of sodium arsenate. One-ml reactions contained the following:

100 mM HEPES, pH 7.2
100 mM NaAsO4, pH 7.2
20 mM $MgCl_2$
250 mM fructose
100 mM $(NH_4)_2SO_4$
100 µl E. coli crude extract (2.8 mg/ml total protein)

The reaction was incubated at 50° C. for 24 hours and analyzed for the presence of glucosamine. Controls consisted of reactions without fructose, without crude extract, and with boiled crude extract. No glucosamine was detected in the no fructose control. The control reactions without crude extract and with boiled extract contained about 280 µg/ml. Use of a crude extract made from cells with a cloned overexpressed glucoseamine-6-phosphate deaminase produced about 1300 ug/ml. Use of a crude extract made from untransformed cells (i.e. the cells did not contain the cloned glucosamine-6-phosphate deaminase) resulted in production of about 290 ug/ml glucosamine. This is about a 100-fold increase in fructose to glucosamine activity in the crude extract made from cells with a cloned overexpressed glucoseamine-6-phosphate deaminase.

Having now fully described the invention, it will be understood by those of ordinary skill in the art that the same can be performed within a wide and equivalent range of conditions, formulations and other parameters without effecting the scope of the invention or any embodiment thereof. All patents and publications cited herein are fully incorporated by reference herein in their entirety.

What is claimed is:

1. A cell-free method of producing glucosamine-6-phosphate from starch, maltodextrin or glycogen comprising incubating starch, maltodextrin or glycogen with an ammonium source in a reaction mix comprising a cellular extract comprising glucosamine-6-phosphate deaminase activity.

2. The method of claim 1, wherein said cellular extract comprises glucosamine-6-phosphate deaminase.

3. The method of claim 1, wherein said extract is a eukaryotic cell or bacterial cell extract.

4. The method of claim 3, wherein said cellular extract is an E. coli extract.

5. The method of claim 1, wherein said cellular extract is prepared by disrupting the cells, removing cellular debris and performing an ammonium sulfate precipitation and collecting the precipitate produced between 30% and 50% ammonium sulfate saturation.

6. The method of claim 1, wherein said starch is selected from the group consisting of soluble starch, corn starch, potato starch, rice starch and wheat starch.

7. The method of claim 1, wherein said glycogen is selected from the group consisting of rabbit liver glycogen, bovine liver glycogen, mussel glycogen and oyster glycogen.

8. The method of claim 1, wherein said maltodextrin is maltodextrin 10.

9. The method of claim 1, wherein said reaction mix further comprises one or more of a phosphorylase, phosphoglucomutase, glucose-1,6-bisphosphate and phosphoglucose isomerase.

10. The method of claim 1, wherein said reaction mix comprises:

a phosphate source;

soluble starch;

KCl;

an ammonium source;

a magnesium source;

glucose-1,6-bisphosphate;

a phosphorylase;

phosphoglucomutase;

phosphoglucose isomerase; and

E. coli extract.

* * * * *

SEQUENCE LISTING

<160> NUMBER OF SEQ ID NOS: 2

<210> SEQ ID NO 1
<211> LENGTH: 36
<212> TYPE: DNA
<213> ORGANISM: Artificial Sequence
<220> FEATURE:
<223> OTHER INFORMATION: Primer used in construction of nagB expression
      plasmid

<400> SEQUENCE: 1
catctagaat tcatgagact gatccccctg actacc                                 36

<210> SEQ ID NO 2
<211> LENGTH: 30
<212> TYPE: DNA
<213> ORGANISM: Artificial Sequence
<220> FEATURE:
<223> OTHER INFORMATION: Primer used in construction of nagB expression
      plasmid

<400> SEQUENCE: 2
catctaaagc ttcaaggagc cagggcaggg                                        30